United States Patent
Durairaaj et al.

(10) Patent No.: US 9,404,139 B2
(45) Date of Patent: Aug. 2, 2016

(54) MUTATED CEPHALOSPORIN HYDROXYLASE AND ITS APPLICATION IN DEACETYLCEPHALOSPORANIC ACID SYNTHESIS

(71) Applicant: ORCHID CHEMICALS & PHARMACEUTICALS LIMITED, Chennai, Tamil Nadu (IN)

(72) Inventors: Micheal Durairaaj, Chennai (IN); Ramanan Thirumoorthy, Chennai (IN); Kanhu Charan Mishra, Chennai (IN); Thangadurai Chinnathambi, Chennai (IN); Cavery Manian Krishnan, Chennai (IN); Padma Rajasekaran, Chennai (IN); Sugumar Subramani, Chennai (IN); Kavitha Daffrose Selvaraj, Chennai (IN); Nataraj Balakrishnan, Chennai (IN); Sathish Ravikumar Chakravarthy, Chennai (IN); Arulmozhi Natrajan Madhiyazhagan, Chennai (IN)

(73) Assignee: ORCHID CHEMICALS & PHARMACEUTICALS LIMITED, Chennai (IN)

( * ) Notice: Subject to any disclaimer, the term of this patent is extended or adjusted under 35 U.S.C. 154(b) by 0 days.

(21) Appl. No.: 14/371,402

(22) PCT Filed: Jan. 9, 2013

(86) PCT No.: PCT/IB2013/050176
§ 371 (c)(1),
(2) Date: Jul. 9, 2014

(87) PCT Pub. No.: WO2013/105030
PCT Pub. Date: Jul. 18, 2013

(65) Prior Publication Data
US 2015/0240282 A1    Aug. 27, 2015

(30) Foreign Application Priority Data
Jan. 10, 2012    (IN) .............................. 105/CHE/2012

(51) Int. Cl.
*C12P 35/06*    (2006.01)
*C12N 9/02*    (2006.01)
*C12N 15/06*    (2006.01)
*C12P 35/00*    (2006.01)

(52) U.S. Cl.
CPC ............... *C12P 35/00* (2013.01); *C12N 9/0071* (2013.01); *C12P 35/06* (2013.01); *Y02P 20/52* (2015.11)

(58) Field of Classification Search
CPC ....... C12P 35/00; C12P 37/00; C12N 9/0071; C12N 15/76
USPC ........... 435/47, 49, 254.5, 252.35, 320.1, 189
See application file for complete search history.

(56) References Cited

U.S. PATENT DOCUMENTS

| | | | |
|---|---|---|---|
| 5,424,196 A | 6/1995 | Cambiaghi et al. | |
| 6,180,361 B1 | 1/2001 | Ingolia et al. | |

FOREIGN PATENT DOCUMENTS

| | | |
|---|---|---|
| EP | 465189 A2 | 1/1992 |
| IN | 445/CHE/2007 | 11/2008 |
| WO | WO 2008/107782 A2 | 9/2008 |

OTHER PUBLICATIONS

Aharonowitz et al., Penicillin and Cephalosporin Biosynthetic Genes: Structure, Organization, Regulation, and Evolution, Annu. Rev. Microbiol. 46: 461-495, 1992.
Brakhage et al., Molecular Regulation of b-Lactam Biosynthesis in Filamentous Fungi Microbiology and Molecular Biology Reviews 62: 547-585, 1998.
Jensen et al., Deacetoxycephalosporin C Synthetase and Deacetoxycephalosporin C Hydroxylase are Two Separate Enzymes in Streptomyces Clavuligerus , Journal of Antibiotics, 38, 263-265, 1985.
Dotzlaf et al., Copurification and Characterization of Deacetoxycephalosporin C Synthetase/Hydroxylase from Cephalosporium acremonium , Journal of Bacteriology, 169, 1611-1618, 1987.
Samson et al., Cloning and Expression of the Fungal Expandase / Hydroxylase Gene involved in Cephalosporin Biosynthesis, Nature Biotechnology, 5, 1207-1215, 1987.
Kovacevic et al., Cloning and Sequencing of the 1-Lactam Hydroxylase Gene (cefF) from Streptomyces clavuligerus: Gene Duplication May Have Led to Separate Hydroxylase and Expandase Activities in the Actinomycetes, Journal of Bacteriology, 173, 398-400, 1991.
Lloyd et al. Controlling the Substrate Selectivity of Deacetoxycephalosporin/deacetylcephalosporin C Synthase , Journal of Biological Chemistry, 279, 15420-15426, 2004.
Baker et al., Deacetoxycephalosporin C Hydroxylase of Streptomyces clavuligerus, Journal of Biological Chemistry 266, 5087-5093, 1991.

(Continued)

*Primary Examiner* — Md. Younus Meah
(74) *Attorney, Agent, or Firm* — Oliff PLC

(57) ABSTRACT

A mutant hydroxylase with increased activity and greater substrate specificity towards phenylacetyl-7-ADCA derivatives for the production of phenylacetyl-7-HACA derivatives, which carries one or more amino acid modification at residue positions when compared with certain wild type hydroxylase from certain groups of residues. Also disclosed is a process for the preparation of deacetyl cephalosporanic acid from the corresponding deacetoxy cephalosporanic acid that includes an enzyme of the present invention. Also provided is a method for the production and processing of such enzymes.

9 Claims, 1 Drawing Sheet

(56) References Cited

OTHER PUBLICATIONS

Coque et al., Characterization of the cefF gene of *Nocardia lactaindurans* encoding a 3'-methylcephem hydroxylase different from the 7-cephem hydroxylase, Applied Microbiology and Biotechnology 44, 605-609, 1996.

Cirino et al., Generating mutant libraries using error-prone PCR, Methods in Molecular Biology. 231, 3-9, 2003.
Joern et al., DNA shuffling, Methods in Molecular Biology.231:85-89, 2003.
Georgescu et al., Saturation mutagenesis, Methods in Molecular Biology 231:75-83, 2003.
Miyazaki et al., Creating random mutagenesis libraries bymegaprimer PCR of whole plasmid (MEGAWHOP), Methods in Molecular Biology. 231: 23-28, 2003.

Figure 1: Alignment of *cef*F (SEQ ID NO 1)

```
MADTPVPIFNLAALREGADQEKFRECVTGMGVFYLTGYGAGDKDHRLATDTAMDFFANGT
EAEKAAVTTDVPTMRRGYSALEAESTAQVTRTGSYTDYSMSFSMGISGNVFPSPEFERVW
EPRRMAPHYDLSIITFIHQTPCANGFVSLQAEIGGELVSLPVVEDAVVVMCGAMAPLATQ
GALPAPRHHVRSPGAGMREGSDRTSSVFFLRPTTDFSFSVAKARSYGLAVDLDMETATFG
DWIGTNYVTMHAKNEPQAG
```

Figure 2: Nucleotide sequence and their corresponding amino acid sequence (SEQ ID NO 1)

```
1    atggcggacacgcccgtaccgatcttcaacctcgccgcactgcgggaaggcgccgatcag
     M   A   D   T   P   V   P   I   F   N   L   A   A   L   R   E   G   A   D   Q
61   gagaagttccgcgagtgcgtgaccgggatgggggtcttctacctcaccgggtacggcgcc
     E   K   F   R   E   C   V   T   G   M   G   V   F   Y   L   T   G   Y   G   A
121  ggggataaggaccaccggctggccacggacacggcgatggacttcttcgcgaacggcacc
     G   D   K   D   H   R   L   A   T   D   T   A   M   D   F   F   A   N   G   T
181  gaggccgagaaggcggccgtgaccacggacgtcccgaccatgcggcgcggctactccgcg
     E   A   E   K   A   A   V   T   T   D   V   P   T   M   R   R   G   Y   S   A
241  ctggaggccgagagcaccgcccaggtgaccaggaccggttcctacacggactactcgatg
     L   E   A   E   S   T   A   Q   V   T   R   T   G   S   Y   T   D   Y   S   M
301  tccttctccatgggcatctcgggcaacgtcttccctcgccggagttcgagcgggtgtgg
     S   F   S   M   G   I   S   G   N   V   F   P   S   P   E   F   E   R   V   W
361  acggagtacttcgacaagctctacgcggcggcccaggagacggcgcggctggtgctgacc
     T   E   Y   F   D   K   L   Y   A   A   A   Q   E   T   A   R   L   V   L   T
421  gcgagcggcggctatgacgcggagatcgtcggaagcctggacgagctgctggacgccgac
     A   S   G   G   Y   D   A   E   I   V   G   S   L   D   E   L   L   D   A   D
481  cccgtgctgcggctgcggtacttccccgaggtgcccgagcaccggtccgccgagcacgag
     P   V   L   R   L   R   Y   F   P   E   V   P   E   H   R   S   A   E   H   E
541  ccgcgccggatggccccgcactacgacctgtcgatcatccttcatccaccagacgccg
     P   R   R   M   A   P   H   Y   D   L   S   I   I   T   F   I   H   Q   T   P
601  tgcgccaacggcttcgtcagcctccaggccgagatcggcggcgaactggtgagcctgccc
     C   A   N   G   F   V   S   L   Q   A   E   I   G   G   E   L   V   S   L   P
661  gtcgtggaggacgccgtcgtcgtgatgtgcggcgcgatggccccgctggcgacccaggc
     V   V   E   D   A   V   V   V   M   C   G   A   M   A   P   L   A   T   Q   G
721  gcgctgcccgcgccccggcaccacgtccggtccccggcgccggtatgcgcgagggcagc
     A   L   P   A   P   R   H   H   V   R   S   P   G   A   G   M   R   E   G   S
781  gaccgcacgtcgagcgtcttcttcctgcgccccacgaccgacttctcgttctcggtggcc
     D   R   T   S   S   V   F   F   L   R   P   T   T   D   F   S   F   S   V   A
841  aaggcccgcagctacggcctcgccgtcgacctcgacatggagacggccaccttcggcgac
     K   A   R   S   Y   G   L   A   V   D   L   D   M   E   T   A   T   F   G   D
901  tggatcggcaccaactacgtcaccatgcacgcgaagaacgagccgcaggccgga    954
     W   I   G   T   N   Y   V   T   M   H   A   K   N   E   P   Q   A   G
```

MUTATED CEPHALOSPORIN HYDROXYLASE AND ITS APPLICATION IN DEACETYLCEPHALOSPORANIC ACID SYNTHESIS

FIELD OF THE INVENTION

The present invention relates to a modified/mutated cephalosporin hydroxylase from *Streptomyces clavuligerus* having better hydroxylation activity and increased specificity towards compound of formula (II), which includes but not limited to phenylacetyl-7-amino deacetoxy cephalosporanic acid (phenylacetyl-7-ADCA) and deacetoxy cephalosporin C (DAOC).

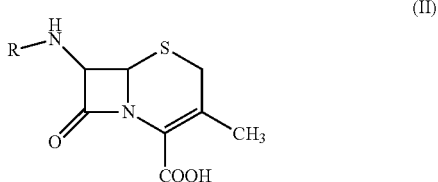

wherein R represents, but not limited to, hydrogen, phenylacetyl, phenoxyacetyl, aminoadipoyl, glutaryl or any other suitable group.

The present invention also describes a bioprocess for preparing cephalosporanic acid of general Formula I by hydroxylating the corresponding compound of formula (II) using mutated cephalosporin hydroxylase of present invention

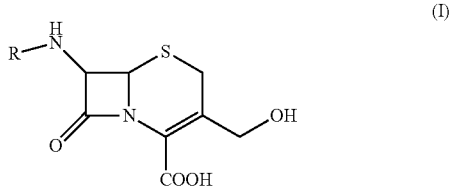

wherein R represents the same as described above. The said process is carried in the presence of α-ketoglutaric acid and ascorbic acid, It also further describes a method for expressing and processing the enzyme cephalosporin hydroxylase for the said reaction. The modified cephalosporin hydroxylase from *Streptomyces clavuligerus* (*S. clavuligerus*) and the bioprocess for synthesis of deacetyl cephalosporanic acid are useful in the process for the preparation of 7-amino cephalosporanic acid (7-ACA), deacetyl-7-ACA (7-HACA), 7-phenylacetamido deacetyl cephalosporanic acid (phenylacetyl-7-HACA), p-methoxybenzyl-7-phenylacetamido-3-chloromethyl cepham-4-carboxylate (GCLE), 7-amino-3-vinyl-4-cephalosporanic acid (CAVA), etc.

BACKGROUND OF THE INVENTION

β-Lactam antibiotics such as Penicillins and Cephalosporins are widely used for the treatment of a variety of infectious diseases. As Cephalosporins offer better protection than Penicillins particularly against resistant organisms, significant thrust has been given to derivatizations of Cephalosporins to broaden their spectrum and enhance their efficacy. 7-ADCA (7-Amino deacetoxy cephalosporanic acid), 7-HACA and 7-ACA serve as core intermediates for the synthesis of numerous semisynthetic cephalosporins such as Cephradine, Cephalexin, Cephadroxyl, Cefazolin, Cefotaxime, Ceftriaxone, Cefepime, Cefoperazone, Cefuroxime, Cefoxitin and the like. Currently, 7-ACA is derived from Cephalosporin C by the cleavage of the 7-aminoadipoyl side chain by a two stage enzymatic process (U.S. Pat. No. 5,424,196) and 7-ADCA is derived from the hydrolysis of phenylacetyl-7-ADCA by Penicillin G amidase, wherein the phenylacetyl-7-ADCA is manufactured by conventional chemistry of ring expansion of Penicillin G. 7-ADCA or ceph G being cheaper than 7-ACA or Ceph C respectively, a process to viably convert 7-ADCA with or without a substituent at 7-amino position, like phenyl acetyl group, to the corresponding deacetyl cephalosporanic acid, would provide a cheaper alternate to HACA.

Native Penicillins and Cephalosporins are produced by a variety of bacteria and fungal organisms and significant progress has been made in understanding their regulatory architecture (Aharonowitz, Y., et al., Annu. Rev. Microbiol. 46: 461-495, 1992; Axel A. Brakhage, Microbiol. Mol. Biol. Rev. 62: 547-585, 1998). Three amino acids, L-valine, L-α-amino adipate and L-cysteine condense to form the tripeptide δ-(L-α-aminoadipoyl)-L-cysteinyl-D-Valine which then, gets cyclized to form isopenicillin N. In the case of penicillin producers, isopenicillin N gets converted to penicillin G, penicillin V, etc. The biosynthesis of cephalosporin by epimerization of isopenicillin N to penicillin N in organisms such as *C. acremonium, S. clavuligerus*, etc leads to cephem compounds such as cephalosporin C and Cephamycin C. The rate limiting or rather, the committed step in the biosynthesis of Cephalosporins is the expansion of the five-membered thiazolidine ring of Penicillin N to a six-membered dihydrothiazine ring of deacetoxy Cephalosporin C (DAOC). In prokaryotes such as *Streptomyces clavuligerus*, the ring-expansion step of Penicillin N is catalyzed by an enzyme called deacetoxy cephalosporin C synthase (DAOCS or cefE or expandase) and hydroxylation of DAOC is carried out by cephalosporin hydroxylase (deacetyl cephalosporin C synthase or DACS or cefF or hydroxylase) (Jensen S. E. et al., Journal of Antibiotics, 38, 263-265, 1985). In eukaryotic organisms such as *Cephalosporium acremonium*, both of these reactions are catalysed by a single bifunctional enzyme DAOCS-DACS (expandase-hydroxylase or cefEF) (Dotzlaf, J. E. and Yeh, W. K., Journal of Bacteriology, 169, 1611-1618, 1987). Subsequently, deacetyl cephalosporin C (DAC) gets acetylated to Cephalosporin C in *Cephalosporium acremonium*, while in bacteria such as *Streptomyces clavuligerus*, further modifications occur resulting in Cephamycin C.

The cefEF gene that codes for 332 amino acids encodes the expandase-hydroxylase in *C. acremonium* (Samson, S. M., et al., Nature Biotechnology, 5, 1207-1215, 1987).

The deacetyl cephalosporin C synthase gene (cefF) has been cloned and sequenced from *S. clavuligerus* and it encodes 318 amino acids (Kovacevic, S. and Miller, J. R., Journal of Bacteriology, 173, 398-400, 1991). The hydroxylase has 54% amino acid sequence identity with that of expandase-hydroxylase of *C. acremonium*. The expandase, expandase-hydroxylase and hydroxylase enzymes are iron (II) and α-ketoglutarate dependent oxygenases and they are part of a subfamily of the mononuclear ferrous enzymes.

Penicillin N is the natural substrate for expandase and expandase-hydroxylase and DAOC is the substrate for hydroxylase. However, altered substrate specificity has been detected for expandase-hydroxylase for different substrates such as Penicillin G, Penicillin V, 6-α-Methylpenicillin N and adipoyl-6-APA (Lloyd et. al. Journal of Biological Chemistry, 279, 15420-15426, 2004). As a result, development of green technologies for the manufacture of Cephalosporin intermediates, thus, narrowed down to these enzymes. However, these enzymes show poor capability to convert readily available substrates such as phenylacetyl-7-ADCA and hence, engineering them for commercial applications is required. WO 2008/107782 (445/CHE/2007) describes such manipulations for hydroxylase and its use in the bioprocess for the preparation of compound of formula (I), some of the strains obtained according to this patent like MTCC 5739, MTCC 5741, MTCC 5746 to MTCC 5749 are not industrially scalable due to the poor hydroxylase activity and hence still it is required to identify better hydroxylase mutant in view of industrial production.

Also in publications like Baker, B. J., et al., Journal of Biological Chemistry 266, 5087-5093, 1991; Coque, J. J. R., et al., Applied Microbiology and Biotechnology 44, 605-609, 1996, conversion of 7-aminoadipoyl deacetoxy cephalosporanic acid to the corresponding deacetyl cephalosporanic acid has been described. When tested these methods did not convert more than 5% of the substrate at very low concentrations. These methods were thus not practical and scalable. No prior art discloses a scalable method for hydroxylation of deacetoxy cephalosporins.

EP 465189 provides the DNA compounds that encode hydroxylase activity of S. clavuligerus. This patent discloses the method for expressing hydroxylase activity of S. clavuligerus in a recombinant host cell. The DNA compound that encodes hydroxylase activity was isolated form S. clavuligerus genomic DNA and it is used to construct recombinant DNA expression vector called pOW399. The cloned hydroxylase gene is used in the hydroxylation of cephalosporin compounds; however the activity of enzyme is unsatisfactory for industrial manufacturing.

U.S. Pat. No. 6,180,361 deals about DNA compounds, recombinant DNA cloning and expression vectors that encode DAOCS and DACS activity. The DNA compound that encodes the DACS/DAOCS activities was isolated from *Cephalosporium acremonium* genomic DNA and used to construct recombinant DNA expression vectors. This invention also discloses a method for expressing a Cephalosporium deacetoxycephalosporin C synthetase/hydroxylase polypeptide in a recombinant host cell.

Hence there is a need to identify a cephalosporin hydroxylase with enhanced activity for hydroxylation of compound of formula (II), which is cost effective and industrially scalable. As native cephalosporin hydroxylase shows poor affinity for compound of Formula (II) and industrial utility demands development of modified hydroxylase to enhance its activity. As a result, current invention is related to the development of modified hydroxylase from *S. clavuligerus* having increased substrate specificity for substrates such as compound of Formula (II), when compared with the wild-type hydroxylase. Current invention also provides a scalable process for the hydroxylation of deacetoxy cephalosporanic acid catalyzed by the modified cephalosporin hydroxylase or any α-ketoglutaric acid dependant hydroxylase.

DESCRIPTION OF THE FIGURE

FIG. 1: Wild-type amino acid sequence of hydroxylase from *S. clavuligerus* is given in SEQ ID No: 1.

FIG. 2: Wild-type nucleotide and amino acid sequence of hydroxylase from *S. clavuligerus* is given in SEQ ID No: 1.

OBJECTIVE OF THE INVENTION

An object of this invention is to provide a modified/mutated hydroxylase with improved capability for hydroxylation than that occurs in the natural wild type hydroxylase.

Another object of this invention is to provide a modified hydroxylase having increased hydroxylation activity on substrates compound of Formula (II) like phenylacetyl-7-ADCA.

Yet another object of this invention is to provide a process for the production of deacetyl cephalosporanic acids from the respective deacetoxy cephalosporanic acids catalyzed by the enzyme cephalosporin hydroxylase.

Still another object of this invention is to provide a method for the production and processing of cephalosporin hydroxylase for use in the industrial production of Compound of formula (I), which is an intermediate for the preparation of number of cephalosporin compounds.

SUMMARY OF THE INVENTION

Accordingly, the present invention provides a mutated cephalosporin hydroxylase from *S. clavuligerus*, which comprises an amino acid substitution at one or more amino acid residues corresponding to the wild type cephalosporin hydroxylase (*Streptomyces clavuligerus*) selected from Proline at position 7, Alanine at position 40, Threonine at position 51, Methionine at position 53, Glutamic acid at position 82, Arginine at position 91, Threonine at position 96, Glycine at position 108, Isoleucine at position 149, Valine at position 171, Alanine at position 177, Arginine at position 182, Methioinine at position 184, Isoleucine at position 193, Phenylalanine at position 195, Glutamine at position 209, Alanine at position 210, Valine at position 226, Methionine at position 233, Leucine at position 236, Alanine at position 237, Alanine at position 241, Valine at position 249, Arginine at position 250, Serine at position 251, Glycine at position 255, Glutamic Acid at position 258, Serine at position 260, Phenylalanine at position 267, Alanine at position 280, Valine at position 307 and Asparagine at position 313.

Specifically, the invention provides a mutated hydroxylase which comprises one or more specific amino acid substitutions selected from P7L, A40V, T51M, M53L, E82D, R91G, T96S, G108D, I149T, V171L, V171M, A177V, R182S, R182W, M184I, I193V, F195L, Q209E, A210V, V226I, M233I, L236V, A237V, A241V, V249I, R250L, S251F, G255D, E258K, S260G, F267L, A280S, V307A, N313D, wherein the residue positions of the amino acid substitutions corresponds to those of a wild-type hydroxylase.

In an aspect mutated hydroxylase of the present invention optionally carries one or more specific amino acid substitution selected from E16G, Y38C, P72L, T90A, T90G, T90D, V150A, P186L, V206I, V221A, V221P, V221H, V221T, M229V, M229I, T273A, T304A, A311M and A311V In another aspect, the invention provides a mutant hydroxylase which comprises combinations of substitutions at one or more residue positions corresponding to those of a wild-type expandase.

The process of invention is to provide a modified cefF gene encoding the mutated deacetyl cephalosporin C synthase (DACS).

Another embodiment of the invention is to provide a cephalosporin hydroxylase protein with modified hydroxylation activity for substrates of formula (II) like phenylacetyl-7-ADCA.

In yet another aspect, the invention provides a recombinant vector specifically an expression vector, which comprises the modified hydroxylase gene.

The present invention further relates to a host strain that contains the expression vector with the modified hydroxylase (cefF) gene.

Another embodiment of the invention is to provide a method for expression of cephalosporin hydroxylase in a host strain that contains the expression vector with the modified hydroxylase (cefF) gene.

Yet another embodiment of the invention is to provide a method to produce and process the said protein for catalyzing the hydroxylation of deacetoxy cephalosporanic acid.

Yet another embodiment of the present invention is to provide a scalable process for the preparation of cephalosporanic acid compound of (formula I)

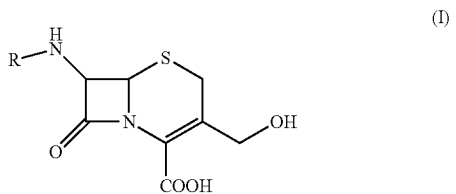

wherein, R represents, but not limited to, hydrogen, phenylacetyl, phenoxyacetyl, aminoadipoyl, glutaryl etc.

The said process comprises contacting the compound of formula (II) in an aqueous medium with modified hydroxylase enzyme of the present invention in the presence of oxygen, α-ketoglutaric acid, ascorbic acid and ferrous sulfate at a temperature in the range of 5-25° C. and pH 5-8.5, preferably 6-8.

The said process is shown in the following scheme:

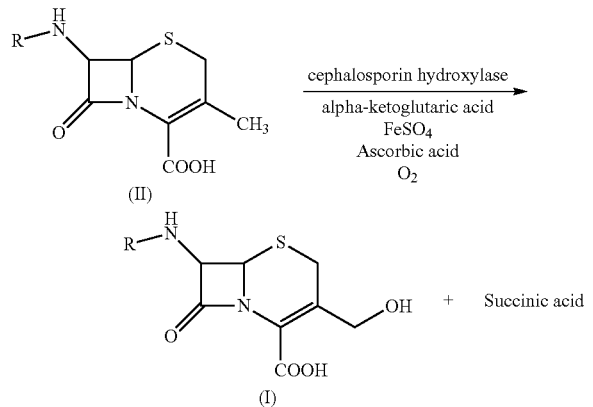

Another aspect of the present invention provides a process for the preparation of deacetyl cephalosporanic acids (formula I) comprising the following steps of:
i) dissolving the deacetoxy cephalosporanic acid;
ii) adding 1-3 mol ratio of α-ketoglutaric acid, 0.1-1 mol ratio of ascorbic acid as compared to the deacetoxy cephalosporanic acid and ferrous sulfate;
iii) adding modified hydroxylase enzyme of the present invention;
iv) carrying out the reaction at pH preferably in the range of 6-8 and temperature between 0-25° C.

DETAILED DESCRIPTION OF THE INVENTION

An embodiment of the present invention is to provide a mutant cephalosporin hydroxylase exhibiting increased activity and greater specificity for substrates such as phenylacetyl-7-ADCA than the wild type hydroxylase from the bacteria S. clavuligerus. This enzyme and the corresponding gene (cefF gene) has been cloned and characterized (Kovacevic S., and Miller J. R., Journal of Bacteriology, 173, 398-400, 1991). The wild-type nucleotide and amino acid sequence of hydroxylase from S. clavuligerus is given in SEQ ID No: 1 (FIG. 2).

Another embodiment of the present invention, a mutated hydroxylase having enhanced hydroxylation activity for substrates such as phenylacetyl-7-ADCA, which comprises an amino acid substitution at one or more amino acid residues corresponding to the wild type hydroxylase for the group of residues consisting of Proline at position 7, Alanine at position 40, Threonine at position 51, Methionine at position 53, Glutamic acid at position 82, Arginine at position 91, Threonine at position 96, Glycine at position 108, Isoleucine at position 149, Valine at position 171, Alanine at position 177, Arginine at position 182, Methioinine at position 184, Isoleucine at position 193, Phenylalanine at position 195, Glutamine at position 209, Alanine at position 210, Valine at position 226, Methionine at position 233, Leucine at position 236, Alanine at position 237, Alanine at position 241, Valine at position 249, Arginine at position 250, Serine at position 251, Glycine at position 255, Glutamic Acid at position 258, Serine at position 260, Phenylalanine at position 267, Alanine at position 280, Valine at position 307 and Asparagine at position 313. Specifically, the invention provides mutants with amino acid substitutions at one or more amino acid residues of P7L, A40V, T51M, M53L, E82D, R91G, T96S, G108D, I149T, V171L, V171M, A177V, R182S, R182W, M184I, I193V, F195L, Q209E, A210V, V226I, M233I, L236V, A237V, A241V, V249I, R250L, S251F, G255D, E258K, S260G, F267L, A280S, V307A, N313D and combinations thereof, wherein the residue positions of the amino acid substitutions corresponds to those of a wild type hydroxylase from S. clavuligerus.

Still another embodiment of the present invention the mutant hydroxylase according to the present invention further carries one or more amino acid modifications at residue positions when compared with the wild type hydroxylase from the following group of residues consisting of Glutamic acid at position 16, Tyrosine at position 38, Proline at position 72, Threonine at position 90, Valine at position 150, Proline at position 186, Valine at position 206, Valine at position 221, Methionine at position 229, Threonine at position 273, Threonine at position 304 and Alanine at position 311. Accordingly, the mutated hydroxylase according to the present invention further carries one or more specific amino acid substitutions selected from E16G, Y38C, P72L, T90A, T90G, T90D, V150A, P186L, V206I, V221A, V221P, V221H, V221T, M229V, M229I, T273A, T304A, A311M, and A311V.

In an another aspect, the invention provides a mutant hydroxylase which comprises combinations of substitutions at one or more residue positions corresponding to those of a wild-type expandase.

The following are the variations in the amino acid residues from the sequence in Seq. ID. NO. 1:
Proline at position 7 is substituted by Leucine
Alanine at position 40 is substituted by Valine
Threonine at position 51 is substituted by Methionine
Methionine at position 53 is substituted by Leucine
Glutamic acid at position 82 is substituted by Aspartic Acid
Arginine at position 91 is substituted by Glycine
Threonine at position 96 is substituted by Serine
Glycine at position 108 is substituted by Aspartic acid
Isoleucine at position 149 is substituted by Threonine
Valine at position 171 is substituted by Leucine
Valine at position 171 is substituted by Methionine Alanine at position 177 is substituted by Valine
Arginine at position 182 is substituted by Tryptophan
Arginine at position 182 is substituted by Serine
Methioinine at position 184 is substituted by Isoleucine
Isoleucine at position 193 is substituted by Valine
Phenylalanine at position 195 is substituted by Leucine
Glutamine at position 209 is substituted by Glutamic Acid
Alanine at position 210 is substituted by Valine
Valine at position 226 is substituted by Isoleucine
Methionine at position 233 is substituted by Isoleucine
Leucine at position 236 is substituted by Valine
Alanine at position 237 is substituted by Valine
Alanine at position 241 is substituted by Valine
Valine at position 249 is substituted by Isoleucine
Arginine at position 250 is substituted by Leucine
Serine at position 251 is substituted by Phenylalanine
Glycine at position 255 is substituted by Aspartic Acid
Glutamic Acid at position 258 is substituted by Lysine
Serine at position 260 is substituted by Glycine
Phenylalanine at position 267 is substituted by Leucine
Alanine at position 280 is substituted by Serine
Valine at position 307 is substituted by Alanine
Asparagine at position 313 is substituted by Aspartic Acid The mutated hydroxylase according the present invention further carries variations in the amino acid residues from the sequence in Seq. ID. NO. 1:

Glutamic acid at position 16 is substituted by Glycine
Tyrosine at position 38 is substituted by Cysteine
Proline at position 72 is substituted by Leucine
Threonine at position 90 is substituted by Alanine
Threonine at position 90 is substituted by Glycine
Threonine at position 90 is substituted by Aspartic acid
Valine at position 150 is substituted by Alanine
Proline at position 186 is substituted by Leucine
Valine at position 206 is substituted by Isoleucine
Valine at position 221 is substituted by Proline
Valine at position 221 is substituted by Histidine
Valine at position 221 is substituted by Alanine
Valine at position 221 is substituted by Threonine
Methionine at position 229 is substituted by Isoleucine
Methionine at position 229 is substituted by Valine
Threonine at position 273 is substituted by Alanine
Threonine at position 304 is substituted by Glycine
Threonine at position 304 is substituted by Isoleucine
Threonine at position 304 is substituted by Leucine
Threonine at position 304 is substituted by Valine
Alanine at position 311 is substituted by Methionine
Alanine at position 311 is substituted by Valine In one more embodiment of the present invention, the modified hydroxylase according to the present invention having following specific amino acid substitution at amino acid residues corresponding to the wild type hydroxylase for the group of residues Proline at position 72 is substituted by Leucine, Threonine at position 90 is substituted by Alanine, Valine at position 206 is substituted by Isoleucine, Alanine at position 210 is substituted by Valine, Alanine at position 311 is substituted by Valine (MTCC 5740)

Proline at position 7 is substituted by Leucine, Proline at position 72 is substituted by Leucine, Threonine at position 90 is substituted by Alanine, Alanine at position 237 is substituted by Valine, Alanine at position 311 is substituted by Valine (MTCC 5742)

Threonine at position 51 is substituted by Methionine, Proline at position 72 is substituted by Leucine, Threonine at position 90 is substituted by Alanine, Alanine at position 311 is substituted by Valine (MTCC 5743)

Alanine at position 40 is substituted by Valine, Proline at position 72 is substituted by Leucine, Threonine at position 90 is substituted by Alanine, Alanine at position 311 is substituted by Valine (MTCC 5744)

Proline at position 72 is substituted by Leucine, Threonine at position 90 is substituted by Alanine, Alanine at position 237 is substituted by Valine, Alanine at position 311 is substituted by Valine (MTCC 5745)

Proline at position 72 is substituted by Leucine, Threonine at position 90 is substituted by Alanine, Methionine at position 233 is substituted by Isoleucine, Alanine at position 311 is substituted by Valine (MTCC 5750)

Proline at position 72 is substituted by Leucine, Threonine at position 90 is substituted by Alanine, Glutamic acid at position 258 is substituted by Lysine, Alanine at position 311 is substituted by Valine (MTCC 5751)

Proline at position 72 is substituted by Leucine, Threonine at position 90 is substituted by Alanine, Phenylalanine at position 195 is substituted by Leucine, Alanine at position 311 is substituted by Valine (MTCC 5752)

Proline at position 72 is substituted by Leucine, Threonine at position 90 is substituted by Alanine, Arginine at position 250 is substituted by Leucine, Alanine at position 311 is substituted by Valine (MTCC 5753)

Proline at position 72 is substituted by Leucine, Threonine at position 90 is substituted by Alanine, Valine at position 226 is substituted by Isoleucine, Alanine at position 311 is substituted by Valine (MTCC 5754)

Proline at position 72 is substituted by Leucine, Threonine at position 90 is substituted by Alanine, Valine at position 206 is substituted by Isoleucine, Alanine at position 210 is substituted by Valine, Threonine at position 273 is substituted by Alanine, Alanine at position 311 is substituted by Valine Proline at position 7 is substituted by Leucine, Proline at position 72 is substituted by Leucine, Threonine at position 90 is substituted by Alanine, Alanine at position 237 is substituted by Valine, Threonine at position 273 is substituted by Alanine, Alanine at position 311 is substituted by Valine Proline at position 7 is substituted by Leucine, Proline at position 72 is substituted by Leucine, Threonine at position 90 is substituted by Alanine, Threonine at position 273 is substituted by Alanine, Alanine at position 311 is substituted by Valine Proline at position 72 is substituted by Leucine, Threonine at position 90 is substituted by Alanine, Alanine at position 237 is substituted by Valine, Threonine at position 273 is substituted by Alanine, Alanine at position 311 is substituted by Valine Threonine at position 51 is substituted by Methionine, Proline at position 72 is substituted by Leucine, Threonine at position 90 is substituted by Alanine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Threonine at position 273 is substituted by Alanine, Alanine at position 311 is substituted by Valine Proline at position 72 is substituted by Leucine, Threonine at position 90 is substituted by Glycine, Alanine at position 237 is substituted by Valine, Threonine at position 273 is substituted by Alanine, Alanine at position 311 is substituted by Valine Threonine at position 51 is substituted by Methionine, Proline at position 72 is substituted by Leucine, Threonine at position 90 is substituted by Alanine, Alanine at position 237 is substituted by Valine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Alanine at position 237 is substituted by Valine, Threonine at position 273 is substituted by Alanine, Alanine at position 311 is substituted by Valine Threonine at position 51 is substituted by Methionine, Proline at position 72 is substituted by Leucine, Threonine at position 90 is substituted by Alanine, Methionine at position 229 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Methionine at position 229 is substituted by Isoleucine, Threonine at position 273 is substituted by Alanine, Alanine at position 311 is substituted by Valine (MTCC 5755)

Proline at position 72 is substituted by Leucine, Threonine at position 90 is substituted by Alanine, Phenylalanine at position 195 is substituted by Leucine, Valine at position 226 is substituted by Isoleucine Alanine at position 311 is substituted by Valine Proline at position 72 is substituted by Leucine, Threonine at position 90 is substituted by Alanine, Phenylalanine at position 195 is substituted by Leucine, Arginine at position 250 is substituted by Leucine, Alanine at position 311 is substituted by Valine Proline at position 72 is substituted by Leucine, Threonine at position 90 is substituted by Alanine, Phenylalanine at position 195 is substituted by Leucine, Glutamic acid at position 258 is substituted by Lysine, Alanine at position 311 is substituted by Valine Alanine at position 40 is substituted by Valine, Proline at position 72 is substituted by Leucine, Threonine at position 90 is substituted by Alanine, Methionine at position 229 is substituted by Isoleucine, Phenylalanine at position 267 is substituted by Leucine, Threonine at position 273 is substituted by Alanine, Alanine at position 311 is substituted by Valine (MTCC 5757)

Alanine at position 40 is substituted by Valine, Proline at position 72 is substituted by Leucine, Threonine at position 90 is substituted by Alanine, Alanine at position 177 is substituted by Valine, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Phenylalanine at position 195 is substituted by Leucine, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Methionine at position 184 is substituted by Isoleucine, Isoleucine at position 193 is substituted by Valine, Methionine at position 229 is substituted by Isoleucine, Threonine at position 273 is substituted by Alanine, Alanine at position 311 is substituted by Valine (MTCC 5756)

Alanine at position 40 is substituted by Valine, Proline at position 72 is substituted by Leucine, Threonine at position 90 is substituted by Alanine, Valine at position 171 is substituted by Leucine, Methionine at position 229 is substituted by Isoleucine, Threonine at position 273 is substituted by Alanine, Alanine at position 311 is substituted by Valine (MTCC 5758)

Alanine at position 40 is substituted by Valine, Proline at position 72 is substituted by Leucine, Threonine at position 90 is substituted by Alanine, Glutamine at position 209 is substituted by Glutamic acid, Methionine at position 229 is substituted by Isoleucine, Valine at position 249 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Glutamine at position 209 is substituted by Glutamic acid, Methionine at position 229 is substituted by Isoleucine, Threonine at position 273 is substituted by Alanine, Alanine at position 311 is substituted by Valine Alanine at position 40 is substituted by Valine, Proline at position 72 is substituted by Leucine, Glutamic acid at position 82 is substituted by Aspartic acid, Threonine at position 90 is substituted by Alanine, Glutamine at position 209 is substituted by Glutamic acid, Methionine at position 229 is substituted by Isoleucine, Leucine at position 236 is substituted by Valine, Valine at position 249 is substituted by Isoleucine, Threonine at position 273 is substituted by Alanine, Alanine at position 311 is substituted by Valine (MTCC 5759)

Alanine at position 40 is substituted by Valine, Proline at position 72 is substituted by Leucine, Threonine at position 90 is substituted by Alanine, Valine at position 221 is substituted by Proline, Methionine at position 229 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 221 is substituted by Histidine, Methionine at position 229 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Arginine at position 182 is substituted by Serine, Methionine at position 229 is substituted by Isoleucine, Threonine at position 273 is substituted by Alanine, Alanine at position 311 is substituted by Valine (MTCC 5760)

Alanine at position 40 is substituted by Valine, Proline at position 72 is substituted by Leucine, Threonine at position 90 is substituted by Alanine, Alanine at position 177 is substituted by Valine, Methionine at position 229 is substituted by Isoleucine, Threonine at position 273 is substituted by Alanine, Alanine at position 311 is substituted by Valine (MTCC 5761)

Alanine at position 40 is substituted by Valine, Proline at position 72 is substituted by Leucine, Threonine at position 90 is substituted by Alanine, Valine at position 171 is substituted by Methionine, Methionine at position 229 is substituted by Isoleucine, Threonine at position 273 is substituted by Alanine, Alanine at position 311 is substituted by Valine (MTCC 5762)

Alanine at position 40 is substituted by Valine, Proline at position 72 is substituted by Leucine, Threonine at position 90 is substituted by Alanine, Methionine at position 229 is substituted by Isoleucine, Serine at position 260 is substituted by Glycine, Threonine at position 273 is substituted by Alanine, Alanine at position 311 is substituted by Valine (MTCC 5763)

Alanine at position 40 is substituted by Valine, Proline at position 72 is substituted by Leucine, Threonine at position 90 is substituted by Alanine, Methionine at position 229 is substituted by Isoleucine, Serine at position 251 is substituted by Phenylalanine, Threonine at position 273 is substituted by Alanine, Alanine at position 311 is substituted by Valine (MTCC 5764)

Alanine at position 40 is substituted by Valine, Proline at position 72 is substituted by Leucine, Threonine at position 90 is substituted by Alanine, Phenylalanine at position 195 is substituted by Leucine, Methionine at position 229 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 226 is substituted by Isoleucine, Methionine at position 229 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Methionine at position 229 is substituted by Isoleucine, Arginine at position 250 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Methionine at position 229 is substituted by Isoleucine, Glutamic acid at position 258 is substituted by Lysine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Methionine at position 229 is substituted by Isoleucine, Methionine at position 233 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Phenylalanine at position 195 is substituted by Leucine, Valine at position 226 is substituted by Isoleucine, Methionine at position 229 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Phenylalanine at position 195 is substituted by Leucine, Arginine at position 250 is substituted by Leucine, Methionine at position 229 is substituted by Isoleucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 226 is substituted by Isoleucine, Methionine at position 229 is substituted by Isoleucine, Arginine at position 250 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Methionine at position 184 is substituted by Isoleucine, Isoleucine at position 193 is substituted by Valine, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Methionine at position 184 is substituted by Isoleucine, Isoleucine at position 193 is substituted by Valine, Methionine at position 233 is substituted by Isoleucine, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 171 is substituted by Leucine, Methionine at position 229 is substituted by Isoleucine, Phenylalanine at position 267 is substituted by Leucine, Threonine at position 273 is substituted by Alanine, Alanine at position 311 is substituted by Valine (MTCC 5765)

Alanine at position 40 is substituted by Valine, Proline at position 72 is substituted by Leucine, Threonine at position 90 is substituted by Alanine, Valine at position 171 is substituted by Leucine, Phenylalanine at position 195 is substituted by Leucine, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 171 is substituted by Leucine, Methionine at position 229 is substituted by Isoleucine, Methionine at position 233 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 171 is substituted by Leucine, Methionine at position 229 is substituted by Isoleucine, Glutamic acid at position 258 is substituted by Lysine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine (MTCC 5766)

Alanine at position 40 is substituted by Valine, Proline at position 72 is substituted by Leucine, Threonine at position 90 is substituted by Alanine, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine, Asparagine at position 313 is substituted by Aspartic acid (MTCC 5767)

Alanine at position 40 is substituted by Valine, Proline at position 72 is substituted by Leucine, Threonine at position 90 is substituted by Alanine, Valine at position 171 is substituted by Leucine, Alanine at position 177 is substituted by Valine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine, Asparagine at position 313 is substituted by Aspartic acid Alanine at position 40 is substituted by Valine, Proline at position 72 is substituted by Leucine, Threonine at position 90 is substituted by Alanine, Arginine at position 91 is substituted by Glycine, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine (MTCC 5768)

Alanine at position 40 is substituted by Valine, Proline at position 72 is substituted by Leucine, Threonine at position 90 is substituted by Alanine, Valine at position 171 is substituted by Leucine, Arginine at position 182 is substituted by Tryptophan, Methionine at position 229 is substituted by Isoleucine, Glycine at position 255 is substituted by Aspartic acid, Phenylalanine at position 267 is substituted by Leucine, Alanine at position 280 is substituted by serine, Threonine at position 273 is substituted by Alanine, Alanine at position 311 is substituted by Valine, (MTCC 5769)

Alanine at position 40 is substituted by Valine, Methionine at position 53 is substituted by Leucine, Proline at position 72 is substituted by Leucine, Threonine at position 90 is substituted by Alanine, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Methionine (MTCC 5770)

Alanine at position 40 is substituted by Valine, Proline at position 72 is substituted by Leucine, Threonine at position 90 is substituted by Alanine, Valine at position 171 is substituted by Leucine, Arginine at position 182 is substituted by Tryptophan, Valine at position 226 is substituted by Isoleucine, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 171 is substituted by Leucine, Arginine at position 182 is substituted by Tryptophan, Methionine at position 229 is substituted by Isoleucine, Alanine at position 241 is substituted by Valine, Phenylalanine at position 267 is substituted by Leucine, Threonine at position 273 is substituted by Alanine, Valine at position 307 is substituted by Alanine, Alanine at position 311 is substituted by Valine (MTCC 5771)

Alanine at position 40 is substituted by Valine, Threonine at position 90 is substituted by Alanine, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Methionine (MTCC 5772)

Alanine at position 40 is substituted by Valine, Proline at position 72 is substituted by Leucine, Threonine at position 90 is substituted by Alanine, Threonine at position 96 is substituted by Serine, Isoleucine at position 149 is substituted by Threonine, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine (MTCC 5773)

Alanine at position 40 is substituted by Valine, Proline at position 72 is substituted by Leucine, Threonine at position 90 is substituted by Alanine, Valine at position 171 is substituted by Leucine, Alanine at position 177 is substituted by Valine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 171 is substituted by Leucine, Arginine at position 182 is substituted by Tryptophan, Methionine at position 229 is substituted by Isoleucine, Serine at position 251 is substituted by Phenylalanine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Valine at position 171 is substituted by Leucine, Arginine at position 182 is substituted by Tryptophan, Methionine at position 229 is substituted by Isoleucine, Serine at position 260 is substituted by Glycine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Arginine at position 91 is substituted by Glycine, Valine at position 171 is substituted by Leucine, Arginine at position 182 is substituted by Tryptophan, Methionine at position 229 is substituted by Isoleucine, Alanine at position 241 is substituted by Valine, Phenylalanine at position 267 is substituted by Leucine, Threonine at position 273 is substituted by Alanine, Valine at position 307 is substituted by Alanine, Alanine at position 311 is substituted by Valine (MTCC 5774)

Alanine at position 40 is substituted by Valine, Proline at position 72 is substituted by Leucine, Threonine at position 90 is substituted by Alanine, Arginine at position 91 is substituted by Glycine, Valine at position 171 is substituted by Leucine, Arginine at position 182 is substituted by Tryptophan, Methionine at position 229 is substituted by Isoleucine, Glycine at position 255 is substituted by Aspartic acid, Phenylalanine at position 267 is substituted by Leucine, Threonine at position 273 is substituted by Alanine, Alanine at position 280 is substituted by serine, Alanine at position 311 is substituted by Valine Alanine at position 40 is substituted by Valine, Proline at position 72 is substituted by Leucine, Threonine at position 90 is substituted by Alanine, Threonine at position 96 is substituted by Serine, Valine at position 171 is substituted by Leucine, Arginine at position 182 is substituted by Tryptophan, Methionine at position 229 is substituted by Isoleucine, Glycine at position 255 is substituted by Aspartic acid, Phenylalanine at position 267 is substituted by Leucine, Threonine at position 273 is substituted by Alanine, Alanine at position 280 is substituted by serine, Alanine at position 311 is substituted by Valine Alanine at position 40 is substituted by Valine, Proline at position 72 is substituted by Leucine, Threonine at position 90 is substituted by Alanine, Threonine at position 96 is substituted by Serine, Valine at position 171 is substituted by Leucine, Arginine at position 182 is substituted by Tryptophan, Methionine at position 229 is substituted by Isoleucine, Alanine at position 241 is substituted by Valine, Phenylalanine at position 267 is substituted by Leucine, Threonine at position 273 is substituted by Alanine, Valine at position 307 is substituted by Alanine, Alanine at position 311 is substituted by Valine Alanine at position 40 is substituted by Valine, Proline at position 72 is substituted by Leucine, Threonine at position 90 is substituted by Alanine, Threonine at position 96 is substituted by Serine, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine Alanine at position 40 is substituted by Valine, Proline at position 72 is substituted by Leucine, Threonine at position 90 is substituted by Alanine, Glycine at position 108 is substituted by Aspartic acid, Valine at position 171 is substituted by Leucine, Arginine at position 182 is substituted by Tryptophan, Methionine at position 229 is substituted by Isoleucine, Phenylalanine at position 267 is substituted by Leucine, Threonine at position 273 is substituted by Alanine, Alanine at position 311 is substituted by Valine (MTCC 5775)

Another embodiment of the invention is to provide an isolated nucleic acid molecule that code for the mutated hydroxylase. According to the invention, this isolated nucleic acid molecule is obtained by mutating the wild type hydroxylase. The mutagenesis technique could be by chemical, error-prone PCR or site-directed approach. The suitable mutagenesis technique can be selected and used for introducing mutations and the mutated nucleic acid molecule can be cloned and expressed and the property of the polypeptide can be studied.

In an aspect of the invention, the mutated nucleic acid may be fused with β-lactamase signal peptide sequence and the fusion protein expressed for enhanced soluble protein expression.

In another aspect of the invention, the mutated nucleic acid molecule may be incorporated into a recombinant vector, which is capable of expression or replication when transferred into a host cell. Expression of the polypeptide can be controlled by a regulatory sequence probably a promoter.

The recombinant vector can be introduced into a host strain to produce the mutated deacetyl cephalosporin C synthase.

The mutated hydroxylase when expressed in the host strain is capable of converting the substrate phenylacetyl-7-ADCA of general formula (II) to phenylacetyl-7-HACA of general formula (I) by hydroxylation. Phenylacetyl-7-HACA can lead to 7-HACA by enzymatic hydrolysis using Pen G amidase or 7-ACA after acetylation by acetyl transferase or suitable chemical conversion followed by enzymatic hydrolysis using Pen G amidase.

According to the present invention, the modified peptide has amino acid sequence different from that of SEQ ID NO: 1. This polypeptide is one, which has hydroxylation activity i.e. catalyze the hydroxylation of 3-methyl side chain of phenylacetyl-7-ADCA to 3-hydroxymethyl. The hydroxylation activity of the polypeptide is modified or increased and also the catalyzing activity for a substrate other than its natural substrate is increased. The invention provides a modified hydroxylase, which has an enhanced catalytic activity or increased specificity for other substrates such as phenylacetyl-7-ADCA when compared with the wild-type hydroxylase.

The polypeptides thus produced from the mutated nucleotide sequence can be used to produce chimeras from portions of other expandase-hydroxylase, expandase and hydroxylase polypeptides.

Polypeptides from the present invention can be purified with varying level of homogeneity and can be used for other purposes.

The invention can be used for the manufacture of modified cephalosporins either as enzymatic or in vivo fermentation based technologies. The detailed procedures, such as transformation and fermentation of such cells, purification and isolation can be found in the literature.

Yet another embodiment of the invention is to provide a method to produce and process the said protein for catalyzing the hydroxylation of deacetoxy cephalosporanic acid.

The *Escherichia coli* BL21 (DE3) strains with modified hydroxylase may be expressed in a flask or fermentor with a pre-induction temperature of 25° C. or lower. Cultivation at higher than 25° C. prior to induction leads to inclusion body and optimal expression in active and soluble form could be found 12-25 hours post induction. The cells may be induced with IPTG and cells harvested anytime between 12 to 30 hours after induction, preferably between 14 to 20 hours and even more preferably 16-20 hours. The induction $OD_{600\,nm}$ can be preferably above, 60 more preferably above 80 and even more preferably above 120.

The cell pellet obtained by fermentation may be lysed after addition of suitable amount of resuspension buffer, by any method not limited to sonication, high pressure homogenization, bead mill, freeze thawing or by addition of any chemical.

According to the invention, the enzyme produced by fermentation may be enriched to obtain enzyme as usable for the catalysis of hydroxylation of deacetoxy cephalosporanic acid, by one or combination of methods. The methods may involve binding of the protein to any matrix with diethylaminoethyl (DEAE) or other weak anion exchange functional group in the presence of Tris buffer or phosphate buffer and eluting with 0.4M sodium chloride (NaCl) solution. Alternate method may involve addition of 0.3% (v/w) of polyethylenimine (PEI) to cell lysate and trapping the enzyme in the formed pellet, or releasing the enzyme from the pellet in to solution with the addition of 0.4M NaCl. In yet another alternate method 0.1% (v/v) PEI may be added stirred for suitable time, preferably 1 hour and centrifuged. To the centrifugate 60% ammonium sulfate (w/w) may be added, followed by stirring over a period of time and centrifuged. The pellet obtained with the active protein may be used for further processing. The active protein thus obtained from any of the above processes may be used as solution or as lyophilized solid or as an immobilized solid or as a granule.

Yet another embodiment of the present invention is to provide a scalable process for the preparation of deacetyl cephalosporanic acids (formula I)

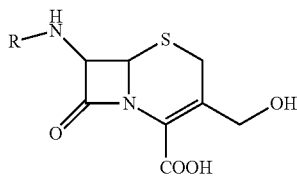

wherein, R can be any group but not limited to, hydrogen, phenylacetyl, aminoadipoyl, glutaryl etc.

Microorganisms from which hydroxylase or expandase/hydroxylase may be obtained but are not limited to are for example *Streptomyces clavuligerus, Nocardia lactamdurans* (formerly known as *Streptomyces lactamdurans*), *Xanthomonas lactamgenus, Flavobacterium* sp, *Streptomyces organanencis, Streptomyces lactamgens, Streptomyces fradiae, Streptomyces griseus, Streptomyces ofivaceus* and *Cephalosporium acremonium.*

The initial concentration of the substrate, deacetoxy cephalosporanic acid in the reaction may be 0.5-10%, preferably 1-10%, even more preferably 2-10%, even more preferably 3-10%, even more preferably 4-10%, and even more preferably 5-10%.

Another aspect of the present invention provides a process for the preparation of deacetyl cephalosporanic acids (formula I) comprising the following steps of:

1) dissolving the deacetoxy cephalosporanic acid of general formula (II) in an aqueous medium;
2) adding 1-3 mol ratio of α-ketoglutaric acid, 0.1-1 mol ratio of ascorbic acid as compared to the deacetoxy cephalosporanic acid and ferrous sulfate;
3) adding the enzyme cephalosporin hydroxylase;
4) carrying out the reaction at pH 5-8.5 and temperature between 5-25° C.;
5) isolating compound of formula (II)

The deacetoxy cephalosporanic acid may be added completely at the start of the reaction or added over a period during the course of the reaction. Any base like ammonia, sodium bicarbonate, sodium hydroxide may be used to solubilize it in water.

1-3 mol ratio of α-ketoglutaric acid may be added to the reaction, preferably 1-2 mol ratio and even more preferably 1-1.5 mol ratio may be all added at start or during the course of the reaction. 0.1-1 mol ratio of ascorbic acid may be added to the reaction; preferably 0.2-0.8 may be all added at start or during the course of the reaction.

The enzyme addition may be used as a solution or as a solid, in free form or trapped or immobilized on a matrix and may be all added at start or during the course of the reaction.

The reaction may be carried out any pH range between 5 and 8.5, preferably between 6.0 and 8, more preferably 6.5 to 7.5 and temperature between 5 and 25° C., preferably between 10 and 25° C. and even more preferably between 15 and 25° C.

The present invention will become apparent with reference to the examples below. The examples described below are given by way of illustration only and are not intended to be any limitation of the present invention.

*Escherichia coli* BL21 (DE3) strains containing modified hydroxylase genes of the present invention were deposited in Microbial Type Culture Collection center Chandigarh, India under Budapest treaty and were assigned accession numbers, (MTCC 5740, MTCC 5742 to MTCC 5745, MTCC 5750 to MTCC 5775) (indicated with ± mark in Table-1).

Materials:

All the chemicals and reagents were purchased either from Sigma-Aldrich Chemicals Pvt. Ltd or USB, USA. Oligonucleotides were synthesized and supplied by Eurofins Genomics, Bangalore, India. Restriction enzymes, pUC19 vector for cloning and strains were obtained from New England Biolabs Inc, USA. pET24a vector for expression, *Escherichia coli* BL21 (DE3) the expression host strain and Bugbuster reagent were from Novagen, USA. *Streptomyces clavuligerus* was obtained from the American Type Culture Collection, USA (ATCC). Bradford reagent was purchased from Biorad, USA. $C_{18}$ columns (50×4.6 mm, 5µ, Xterra) were obtained from Waters, USA. DNeasy Plant mini gDNA isolation Kit and QIAEX II Gel extraction kit were supplied by Qiagen, Germany and growth media components were obtained from Becton Dickinson, USA.

*Streptomyces clavuligerus* Growth Conditions:

The *S. clavuligerus* strain (ATCC No. 27064) was grown on YMG media containing Yeast extract 4 gm, Malt extract 10 gm and Glucose 4 gm made up to 1 liter of distilled water at pH 7. The culture was incubated at 25° C. and 180 rpm for 48 hours. Once the $OD_{600\,nm}$ reached 3, the mycelia were harvested and cell pellets were collected after centrifugation at 16,000 rpm for 15 minutes.

Polymerase Chain Reaction:

Genomic DNA was isolated from the mycelia using the DNeasy Plant mini gDNA isolation kit (Qiagen) as per protocol provided with the kit. The gene coding for the hydroxylase (cefF) (Accession number: M63809) was amplified using 20 pmole of primers 5' GCATATGGCGGACACGC-CCGTACC 3' (SEQ ID NO:3) and 5' CCCGGCTTGAATG-CAACGACGAGCAT 3', (SEQ ID NO:4), 200 µM dNTPs, 10% DMSO, deep vent DNA polymerase buffer, 2U deep vent DNA polymerase enzyme, 1 mM $MgSO_4$ and water in a final reaction volume of 100 PCR condition consists of an initial denaturation for 5 min at 95° C. followed by 24 cycles consisting of denaturation at 95° C. for 40 sec, annealing at 60° C. for 1 min, extension at 72° C. for 5 min with a final extension at 72° C. for 15 min. An amplified product of length of approximately 1 kb of the cefF gene fragment was verified by agarose gel electrophoresis.

Cloning in pUC19 and pET24a:

The hydroxylase gene fragment observed after amplification was purified by QIAEX II Gel extraction kit (Qiagen) and cloned into pUC19 vector through blunt-end ligation using SmaI restriction site to provide pOBTF. Subsequently, the hydroxylase gene fragment was released by digestion with NdeI/EcoRI and ligated into similarly digested pET24a (+) to give pOCPLF vector and transformed into competent *Escherichia coli* BL21 (DE3) strain for further expression.

Generation of β-Lactamase Fusion Protein:

A primer containing the β-lacatamase signal peptide gene and initial codons of cefF gene was obtained (from Sigma Aldrich) and fused with the cefF gene by running primerless PCR for 30 cycles. Subsequently, this PCR product was used as template for another set of PCR (30 cycles) wherein the forward primer had a part of β-lacatamase signal sequence and the reverse primer had the cefF sequence (of the 3' end), amplified. The PCR condition remains the same as described earlier for amplifying cefF gene. The PCR mixture was electrophoresed in an agarose gel and the gene product was extracted from gel using gel extraction kit obtained from Sigma Aldrich, Bangalore. The fused gene product, isolated was cloned into pBSK through blunt-end ligation using SmaI restriction site using standard molecular biology protocols. Subsequently, the β-lacatamase signal—cefF (BF) gene fragment was released by digestion with NcoI & Hind III and ligated into similarly digested pET24a to give pBFP vector and transfor med into competent *Escherichia coli* BL21 (DE3) strain for further expression of the fusion construct. Expression and activity measurements indicated two fold more activity than the corresponding parental construct.

Mutagenesis and Library Creation:

The pOBTF vector served as the initial template for random and site-directed mutagenesis to generate variants of the cefF gene. Random mutagenesis was done amplifying the cefF gene by polymerase chain reaction (PCR) by employing mutagenic conditions that favour incorporation of non-complimentary nucleotides during DNA synthesis by DNA polymerase (Error-prone PCR mutagenesis). This can be achieved by choosing appropriate DNA polymerase (e.g. Taq DNA polymerase has been used in several studies for random mutagenesis) and/or by modifying the composition of the PCR reaction mixture to accentuate the error-prone polymerase activity (e.g. by biasing the concentration of dNTPs instead of using an equimolar mixture of all four dNTPs). The article Cirino P C, et al., *Generating mutant libraries using error-prone PCR*, Methods Mol Biol. 2003; 231: 3-9 and the references therein may be referred for detailed protocol. The mutant copies of cefF genes thus obtained are cloned into the expression vector pET24a and transformed into the expression strain, *E. coli* B121 (DE3) to create a library of clones expressing mutants/variants of cefF protein. Individual colonies obtained in the transformation are grown in 96-well culture plates and stored as glycerol stocks at −80° C. The desired property can also be improved by generating combinations of the mutants obtained by random mutagenesis by employing procedures like DNA shuffling (random combinations) [Joern J M. *DNA shuffling*, Methods Mol Biol. 2003; 231:85-89] and/or site-directed mutagenesis (specific combinations). The mutants can also be further optimized by incorporating amino acids other than the ones obtained through random mutagenesis by procedures like site-saturation mutagenesis and/or site-directed mutagenesis. The detailed protocols can be found in the articles Georgescu R, et al., *Saturation mutagenesis*, Methods Mol Biol. 2003; 231:75-83 and Miyazaki K. *Creating random mutagenesis libraries by megaprimer PCR of whole plasmid (MEGAWHOP)*, Methods Mol Biol. 2003; 231: 23-28 and the references therein. Once a mutant is identified with desired properties (improved activity in this case), it can serve as the template for next round of directed evolution involving some or all the procedures as described above.

Expression of Library Clones for Screening:

Glycerol stocks containing the putative mutant cefF genes in pET24a (+) vector in *E. coli* BL21 (DE3) strain was inoculated in 96-well plate containing LB medium with Kanamycin (75 µg/ml) for overnight growth at 37° C. at 260 rpm. Overnight culture was subcultured again in 96-well deep well plates containing 1 ml LB media and grown at 37° C. till $OD_{600\,nm}$ reached to 0.4 to 0.6 and the induction was carried out with 0.1 mM isopropyl-β-D-thiogalactopyranoside (IPTG). After induction, the culture was allowed to grow for 5 hours at 25° C. and cells was harvested by centrifugation in a micro plate centrifuge at 4,000 rpm for 10 min at 4° C. The pellets were stored at −80° C. till further use.

Assay for Activity Screening:

Enzyme from expressed clones was released using bugbuster reagent and the hydroxylation reaction was assayed with 45 mM α-ketoglutaric acid, 9 mM ascorbate, 0.1 mM ferrous sulfate, 355 mM Tris.HCl and 0.56% phenylacetyl-7-ADCA in a reaction volume of 200 µl at 25° C. for 180 minutes with shaking at 220 rpm. The reaction was quenched with 200 µl of methanol and analyzed by HPLC. Activity data has been tabulated in Table 1 with the wild type enzyme benchmarked as 100%.

High Performance Liquid Chromatography Monitoring of Hydroxylase Activity:

All HPLC data was collected on Shimadzu 2010C. $C_{18}$ Xterra column was equilibrated with buffer containing 3.12 g of sodium phosphate in 800 ml water and 200 ml acetonitrile with pH adjusted to 2.4 using ortho-phosphoric acid. The assay components were eluted using buffer A at a flow rate of 2.5 ml/min. 20 µl of sample was injected and the components were detected at 260 nm. The retention times of the compounds under these conditions are 0.65 min and 1.3 min for phenylacetyl dacetyl-7-ACA and phenylacetyl-7-ADCA respectively.

Large Scale Protein Expression:

Fermentation media was prepared as described by Lee S Y. and Chang H N., Biotechnology Letters, 15, 971-974, 1993.

4-5% seed inoculum grown for 6-8 hours in shake flask in R/2 media was transferred to fermentor and cultivated at 25 degree celcius with an agitation to maintain dissolved oxygen of at least 40%. On depletion of resident glucose, feeding was initiated to maintain residual glucose of 0.1 g/L. On $OD_{600\,nm}$ reaching about 40 to 150, 0.1 mM IPTG was added to induce the protein production. The cells were further cultivated for 12-18 hours post induction and then harvested.

Cell Lysis:

Cell pellet (20 g) from high cell-density fermentation was taken and re-suspended in 200 ml re-suspension buffer (50 mM Tris pH 8.0, 1 mM DTT and 10% glycerol). After complete re-suspension 200 ul of 100 mg/ml lysozyme was added and stirred for 20 min. The cells were lysed by sonication for 15 min, alternatively can be lysed using a homogenizer.

Enzyme Processing:

The enzyme is processed by either one of the methods below or combination of methods thereof.

a) Column Purification:

The cell lysate was centrifuged at 13000 rpm for 15 min, the supernatant was retained and the pellet discarded. The supernatant was column purified as below using AKTA purifier from GE healthcare.

Column: XK26/20

Matrix: DE52 whatmann or any matrix with diethylaminoethyl (DEAE) or weak anion exchange functional group.

Flow rate: 5 m/min

Start buffer: 50 mM Tris pH 8.0, 1 mM DTT and 10% glycerol

Elution buffer: 50 mM Tris pH 8.0, 1 mM DTT and 10% glycerol+0.4M Nacl

The column was washed with 10 column volumes of water and then equilibrated with 10 column volumes of start buffer. The sample was loaded to the column and washed with the start buffer until the flow through showed no UV absorbance. The protein was eluted with the elution buffer.

b) Protein Precipitation by PEI

Method 1: To the lysate 0.3% (v/w) of PEI was added and stirred for 60 min. The sample was centrifuged for 10 min at 4000 rpm, the pellet retained and supernatant discarded.

Method 2: The cell lysate was centrifuged at 13000 rpm for 15 min, the supernatant was retained and the pellet discarded. To the supernatant 0.3% (v/w) of PEI was added and stirred for 60 min. The sample was centrifuged for 10 min at 4000 rpm, the pellet retained and supernatant discarded.

Method 3: The cell lysate was centrifuged at 13000 rpm for 15 min, the supernatant was retained and the pellet discarded. To the supernatant 0.3% (v/w) of PEI was added and stirred for 60 min. The sample was centrifuged for 10 min at 4000 rpm, the pellet retained and supernatant discarded. The pellet was resuspended in elution buffer (50 mM Tris pH 8.0, 1 mM DTT and 10% glycerol+0.4M NaCl) for 15 min then centrifuged at 4000 rpm for 10 min. The supernatant was retained for the reaction.

Ammonium Sulfate Fractionation

Cell pellet (20 g) was taken, re-suspended in 200 ml re-suspension buffer (50 mM Tris pH 8.0, 1 mM DTT and 10% glycerol). After complete re-suspension, 200 µl of lysozyme from 100 mg/ml stock was added and stirred for 20 min. The sample was sonicated (power level 0.5 and amplitude 60%) for 15 min. 0.1% of PEI was added and stirred for 60 min. The sample was centrifuged for 10 min at 4000 rpm, the supernatant taken and the pellet discarded. Ammonium sulfate (60% w/w) was added to the supernatant and stirred for overnight. The solution was then centrifuged at 13000 rpm for 10 min. The pellet with the active protein was used for further reaction. All the above steps were carried out at 4° C.

Protein Lyophilization:

20 g pellet was resuspended in 100 ml of 50 mM buffer, PH 7.0 phosphate buffer with 100 µl of lysozyme (100 mg/ml). The cell suspension was lysed by sonication. The solution centrifuged at 10000 rpm for 30-40 min and the supernatant taken. To this 2.5 ml of PEI (from 10% stock) was added and stirred for 2 hrs. The solution was centrifuged at 10000 rpm for 15 min and to the supernatant 1% of PEG 6000 was added and stirred for 10-30 min. The sample was frozen and set for lyophilization. Lyophilized protein as free flowing solid was obtained in 20-24 hrs.

Reaction Monitoring:

The hydroxylation reaction was carried out using 360 mg phenylacetyl 7-ADCA, 239 mg α-ketoglutaric acid, 95 mg ascorbic acid and 2.64 mg ferrous sulfate using 120 mg of the enzyme, at pH 7.3 in a reaction volume of 20 ml with constant stirring at 15° C. for 300 minutes. Reaction was monitored by HPLC by taking 10 µl of the reaction mix, quenched with 20 µl methanol and 90 µl water, centrifuged and the supernatant analyzed. End point is denoted by the reaction going to 95-97% completion.

TABLE 1

Details of mutants showing improved hydroxylation.
The relative activity of each mutant was compared with the activity of the Wild Type enzyme (FIG. 1), which is set as 100%.

| S. No. | Mutant ID | No of mutations | Mutations | Fold Improvement |
|---|---|---|---|---|
| 1 | G3 | 5 | P72L, T90A, V206I, A210V, A311V | 260% |
| 2 | G56 | 5 | P7L, P72L, T90A, A237V, A311V | 280% |
| 3 | G71 | 4 | T51M, P72L, T90A, A311V | 300% |
| 4 | G73 | 4 | A40V, P72L, T90A, A311V | 320% |
| 5 | G74 | 4 | P72L, T90A, A237V, A311V | 340% |
| 6 | TMD 3G05 | 4 | P72L, T90A, M233I, A311V | 400% |
| 7 | TMD 1A12 | 4 | P72L, T90A, E258K, A311V | 400% |
| 8 | TMD 9B07 | 4 | P72L, T90A, F195L, A311V | 410% |
| 9 | TMD 9B09 | 4 | P72L, T90A, R250L, A311V | 380% |
| 10 | TMD 10F11 | 4 | P72L, T90A, V226I, A311V | 380% |
| 11 | G3Q | 6 | P72L, T90A, V206I, A210V, T273A, A311V | 360% |
| 12 | G56A | 6 | P7L, P72L, T90A, A237V, T273A, A311V | 360% |
| 13 | G56B | 5 | P7L, P72L, T90A, T273A, A311V | 340% |
| 14 | G56C | 5 | P72L, T90A, A237V, T273A, A311V | 280% |
| 15 | G71Q | 5 | T51M, P72L, T90A, T273A, A311V | 360% |
| 16 | G73Q | 5 | A40V, P72L, T90A, T273A, A311V | 360% |
| 17 | G74Q-TG | 5 | P72L, T90G, A237V, T273A, A311V | 340% |
| 18 | G71-G74Q | 6 | T51M, P72L, T90A, A237V, T273A, A311V | 340% |
| 19 | G73-G74Q | 6 | A40V, P72L, T90A, A237V, T273A, A311V | 320% |
| 20 | G71-G40Q | 6 | T51M, P72L, T90A, M229I, T273A, A311V | 420% |
| 21 | G73-G40Q/M | 6 | A40V, P72L, T90A, M229I, T273A, A311V | 340% |
| 22 | G134 | 7 | A40V, P72L, T90A, M229I, F267L, T273A, A311V | 620% |
| 23 | 134 + 177V | 8 | A40V, P72L, T90A, A177V, M229I, F267L, T273A, A311V | 610% |
| 24 | 134 + 195L | 8 | A40V, P72L, T90A, F195L, M229I, F267L, T273A, A311V | 500% |
| 25 | G148 | 8 | A40V, P72L, T90A, M184I, I193V, M229I, T273A, A311V | 620% |
| 26 | G151 | 7 | A40V, P72L, T90A, V171L, M229I, T273A, A311V | 620% |
| 27 | G169 | 8 | A40V, P72L, T90A, Q209E, M229I, V249I, T273A, A311V | 620% |
| 28 | G179 | 7 | A40V, P72L, T90A, Q209E, M229I, T273A, A311V | 620% |

TABLE 1-continued

Details of mutants showing improved hydroxylation.
The relative activity of each mutant was compared with the activity
of the Wild Type enzyme (FIG. 1), which is set as 100%.

| S. No. | Mutant ID | No of mutations | Mutations | Fold Improvement |
|---|---|---|---|---|
| 29 | G182 | 10 | A40V, P72L, E82D, T90A, Q209E, M229I, L236V, V249I, T273A, A311V | 620% |
| 30 | M + V221-A | 7 | A40V, P72L, T90A, V221P, M229I, T273A, A311V | 530% |
| 31 | M + V221-B | 7 | A40V, P72L, T90A, V221H, M229I, T273A, A311V | 530% |
| 32 | M + R182 | 7 | A40V, P72L, T90A, R182S, M229I, T273A, A311V | 580% |
| 33 | M 38A11 | 7 | A40V, P72L, T90A, A177V, M229I, T273A, A311V | 620% |
| 34 | M 38B10 | 7 | A40V, P72L, T90A, V171M, M229I, T273A, A311V | 620% |
| 35 | M 2A11B | 7 | A40V, P72L, T90A, M229I, S260G, T273A, A311V | 660% |
| 36 | M 78C12 | 7 | A40V, P72L, T90A, M229I, S251F, T273A, A311V | 750% |
| 37 | M + 195 | 7 | A40V, P72L, T90A, F195L, M229I, T273A, A311V | 630% |
| 38 | M + 226 | 7 | A40V, P72L, T90A, V226I, M229I, T273A, A311V | 560% |
| 39 | M + 250 | 7 | A40V, P72L, T90A, M229I, R250L, T273A, A311V | 560% |
| 40 | M + 258 | 7 | A40V, P72L, T90A, M229I, E258K, T273A, A311V | 380% |
| 41 | M + 233I | 7 | A40V, P72L, T90A, M229I, T273A, A311V | 360% |
| 42 | M195L + 226V | 8 | A40V, P72L, T90A, F195L, V226I, M229I, T273A, A311V | 540% |
| 43 | M195L + 250R | 8 | A40V, P72L, T90A, F195L, R250L, M229I, T273A, A311V | 380% |
| 44 | M226V + 250R | 8 | A40V, P72L, T90A, V226I, M229I, R250L, T273A, A311V | 340% |
| 45 | P | 9 | A40V, P72L, T90A, M184I, I193V, M229I, F267L, T273A, A311V | 500% |
| 46 | P + 233I | 10 | A40V, P72L, T90A, M184I, I193V, M233I, M229I, F267L, T273A, A311V | 380% |
| 47 | R | 8 | A40V, P72L, T90A, V171L, M229I, F267L, T273A, A311V | 800% |
| 48 | R + 195L | 9 | A40V, P72L, T90A, V171L, F195L, M229I, F267L, T273A, A311V | 680% |
| 49 | R + 233I | 9 | A40V, P72L, T90A, V171L, M229I, M233I, F267L, T273A, A311V | 560% |
| 50 | R + 258E | 9 | A40V, P72L, T90A, V171L, M229I, E258K, F267L, T273A, A311V | 720% |
| 51 | S | 9 | A40V, P72L, T90A, V171L, R182W, M229I, F267L, T273A, A311V | 1000% |
| 52 | G234 | 10 | A40V, P72L, T90A, V171L, R182W, M229I, F267L, T273A, A311V, N313D | 1200% |
| 53 | G234 + 177V | 11 | A40V, P72L, T90A, V171L, A177V, R182W, M229I, F267L, T273A, A311V, N313D | 800% |
| 54 | G248 | 10 | A40V, P72L, T90A, R91G, V171L, R182W, M229I, F267L, T273A, A311V | 1300% |
| 55 | G283 | 11 | A40V, P72L, T90A, V171L, R182W, M229I, G255D, F267L, A280S, T273A, A311V, | 1300% |
| 56 | G295 | 10 | A40V, M53L, P72L, T90A, V171L, R182W, M229I, F267L, T273A, A311M | 1200% |
| 57 | G304 | 10 | A40V, P72L, T90A, V171L, R182W, V226I, M229I, F267L, T273A, A311V | 1100% |
| 58 | G315 | 11 | A40V, P72L, T90A, V171L, R182W, M229I, A241V, F267L, T273A, V307A, A311V | 1500% |
| 59 | G325 | 8 | A40V, T90A, V171L, R182W, M229I, F267L, T273A, A311V | 1200% |
| 60 | G344 | 9 | A40V, P72L, T90A, V171L, R182W, M229I, F267L, T273A, A311M | 1200% |
| 61 | G350 | 11 | A40V, P72L, T90A, T96S, I149T, V171L, R182W, M229I, F267L, T273A, A311V | 1200% |
| 62 | S + 177V | 10 | A40V, P72L, T90A, V171L, A177V, R182W, M229I, F267L, T273A, A311V | 900% |
| 63 | S + 251F | 10 | A40V, P72L, T90A, V171L, R182W, M229I, S251F, F267L, T273A, A311V | 1000% |
| 64 | S + 260G | 10 | A40V, P72L, T90A, V171L, R182W, M229I, S260G, F267L, T273A, A311V | 1000% |
| 65 | T | 12 | A40V, P72L, T90A, R91G, V171L, R182W, M229I, A241V, F267L, T273A, V307A, A311V | 1700% |
| 66 | G248 + G283 | 12 | A40V, P72L, T90A, R91G, V171L, R182W, M229I, G255D, F267L, T273A, A280S, A311V | 1200% |
| 67 | G350 + G283 | 12 | A40V, P72L, T90A, T96S, V171L, R182W, M229I, G255D, F267L, T273A, A280S, A311V | 1300% |
| 68 | G350 + G315 | 12 | A40V, P72L, T90A, T96S, V171L, R182W, M229I, A241V, F267L, T273A, V307A, A311V | 1500% |
| 69 | G350 + S | 10 | A40V, P72L, T90A, T96S, V171L, R182W, M229I, F267L, T273A, A311V | 1200% |
| 70 | GOS3 | 10 | A40V, P72L, T90A, G108D, V171L, R182W, M229I, F267L, T273A, A311V | 1900% |

The above table clearly indicates that the mutated hydroxylase of the present invention has significantly higher hydroxylation activity towards compound of formula (II) than the corresponding wily type. As the mutated hydroxylase of the present invention has more than 10 fold higher activity than the native hydroxylase, the present invention provides bioprocess for the preparation of compound of formula (I) in manufacturing scale at low cost. Because of the identification of the mutated hydroxylase, the present invention provides an eco-friendly green process for the preparation of number of cephalosporin drugs/intermediates.

We claim:

1. A mutant hydroxylase of a wild type hydroxylase having the amino acid sequence set forth in SEQ ID NO: 1, the mutant hydroxylase comprising an amino acid modification of at least one amino acid residue selected from the group consisting of P7, A40, T51, M53, E82, R91, T96, G108, I149, V171, A177, R182, M184, I193, F195, Q209, A210, V226, M233, L236, A237, A241, V249, R250, S251, G255, E258, 5260, F267, A280, V307, and with N313, wherein the said mutant hydroxylase comprises increased hydroxylase activity than that of the wild type hydroxylase of the amino acid sequence of SEQ ID NO: 1.

2. The mutant hydroxylase according to claim 1, further comprising an amino acid modification of at least one amino acid residue selected from the group consisting of E16, Y38, P72, T90, V150, P186, V206, V221, M229, T273, T304, and A311.

3. The mutant hydroxylase of claim 1, comprising at least one amino acid substitution selected from the group consisting of P7L, A40V, T51M, M53L, E82D, R91G, T96S, G108D, I149T, V171L, V171M, A177V, R182S, R182W, M184I, I193V, F195L, Q209E, A210V, V226I, M233I, L236V, A237V, A241V, V249I, R250L, S251F, G255D, E258K, S260G, F267L, A280S, V307A, and N313D.

4. The mutant hydroxylase according to claim 3, further comprising at least one amino acid substitution selected from the group consisting of E16G, Y38C, P72L, T90A, T90G, T90D, V150A, P186L, V206I, V221C, V221A, V221P, V221H, V221T, M229V, M229I, T273A, T304A, A311M, and A311V.

5. The mutant hydroxylase of claim 1, comprising a set of amino acid substitutions selected from the group of sets of amino acid substitutions consisting of:
P72L, T90A, V206I, A210V, A311V;
P7L, P72L, T90A, A237V, A311V;
T51M, P72L, T90A, A311V;
A40V, P72L, T90A, A311V;
P72L, T90A, A237V, A311V;
P72L, T90A, M233I, A311V;
P72L, T90A, E258K, A311V;
P72L, T90A, F195L, A311V;
P72L, T90A, I7250L, A311V;
P72L, T90A, V226I, A311V;
P72L, T90A, V206I, A210V, T273A, A311V;
P7L, P72L, T90A, A237V, T273A, A311V;
P7L, P72L, T90A, T273A, A311V;
P72L, T90A, A237V, T273A, A311V;
T51M, P72L, T90A, T273A, A311V;
A40V, P72L, T90A, T273A, A311V;
P72L, T90G, A237V, T273A, A311V;
T51M, P72L, T90A, A237V, T273A, A311V;
A40V, P72L, T90A, A237V, T273A, A311V;
T51M, P72L, T90A, M229I, T273A, A311V;
A40V, P72L, T90A, M229I, T273A, A311V;
A40V, P72L, T90A, M229I, F267L, T273A, A311V;
A40V, P72L, T90A, A177V, M229I, F267L, T273A, A311V;
A40V, P72L, T90A, F195L, M229I, F267L, T273A, A311V;
A40V, P72L, T90A, M184I, I193V, M229I, T273A, A311V;
A40V, P72L, T90A, V171L, M229I, T273A, A311V;
A40V, P72L, T90A, Q209E, M229I, V249I, T273A, A311V;
A40V, P72L, T90A, Q209E, M229I, T273A, A311V;
A40V, P72L, E82D, T90A, Q209E, M229I, L236V, V249I, T273A, A311V;
A40V, P72L, T90A, V221P, M229I, T273A, A311V;
A40V, P72L, T90A, V221H, M229I, T273A, A311V;
A40V, P72L, T90A, R182S, M229I, T273A, A311V;
A40V, P72L, T90A, A177V, M229I, T273A, A311V;
A40V, P72L, T90A, V171M, M229I, T273A, A311V;
A40V, P72L, T90A, M229I, S260G, T273A, A311V;
A40V, P72L, T90A, M229I, S251F, T273A, A311V;
A40V, P72L, T90A, F195L, M229I, T273A, A311V;
A40V, P72L, T90A, V226I, M229I, T273A, A311V;
A40V, P72L, T90A, M229I, R250L, T273A, A311V;
A40V, P72L, T90A, M229I, E258K, T273A, A311V;
A40V, P72L, T90A, M229I, M233I, T273A, A311V;
A40V, P72L, T90A, F195L, V226I, M229I, T273A, A311V;
A40V, P72L, T90A, F195L, R250L, M229I, T273A, A311V;
A40V, P72L, T90A, V226I, M229I, R250L, T273A, A311V;
A40V, P72L, T90A, M184I, I193V, M229I, F267L, T273A, A311V;
A40V, P72L, T90A, M184I, I193V, M233I, M229I, F267L, T273A, A311V;
A40V, P72L, T90A, V171L, M229I, F267L, T273A, A311V;
A40V, P72L, T90A, V171L, F195L, M229I, F267L, T273A, A311V;
A40V, P72L, T90A, V171L, M229I, M233I, F267L, T273A, A311V;
A40V, P72L, T90A, V171L, M229I, E258K, F267L, T273A, A311V;
A40V, P72L, T90A, V171L, R182W, M229I, F267L, T273A, A311V;
A40V, P72L, T90A, V171 L, R182W, M229I, F267L, T273A, A311V, N313D;
A40V, P72L, T90A, V171L, A177V, R182W, M229I, F267L, T273A, A311V, N313D;
A40V, P72L, T90A, R91G, V171L, R182W, M229I, F267L, T273A, A311V;
A40V, P72L, T90A, V171L, R182W, M229I, G255D, F267L, A280S, T273A, A311V;
A40V, M53L, P72L, T90A, V171L, R182W, M229I, F267L, T273A, A311M;
A40V, P72L, T90A, V171L, R182W, V226I, M229I, F267L, T273A, A311V;
A40V, P72L, T90A, V171L, R182W, M229I, A241V, F267L, T273A, V307A, A311V;
A40V, T90A, V171L, R182W, M229I, F267L, T273A, A311V;
A40V, P72L, T90A, V171L, R182W, M229I, F267L, T273A, A311M;
A40V, P72L, T90A, T96S, I149T, V171L, R182W, M229I, F267L, T273A, A311V;
A40V, P72L, T90A, V171L, A177V, R182W, M229I, F267L, T273A, A311V;
A40V, P72L, T90A, V171L, R182W, M229I, S251F, F267L, T273A, A311V;
A40V, P72L, T90A, V171L, R182W, M229I, S260G, F267L, T273A, A311V;
A40V, P72L, T90A, R91G, V171L, R182W, M229I, A241V, F267L, T273A, V307A, A311V;
A40V, P72L, T90A, R91G, V171L, R182W, M229I, G255D, F267L, T273A, A280S, A311V;
A40V, P72L, T90A, T96S, V171L, R182W, M229I, G255D, F267L, T273A, A280S, A311V;
A40V, P72L, T90A, T96S, V171L, R182W, M229I, A241V, F267L, T273A, V307A, A311V;
A40V, P72L, T90A, T96S, V171L, R182W, M229I, F267L, T273A, A311V; and
A40V, P72L, T90A, G108D, V171L, R182W, M229I, F267L, T273A, A311V.

6. The mutant hydroxylase of claim 1 comprising a set of amino acid substitutions selected from the group of sets of amino acid substitutions consisting of:
P72L, T90A, V206I, A210V, A311V;
P7L, P72L, T90A, A237V, A311V;
T51M, P72L, T90A, A311V;
A40V, P72L, T90A, A311V;
P72L, T90A, A237V, A311V;
P72L, T90A, M233I, A311V;
P72L, T90A, E258K, A311V;
P72L, T90A, F195L, A311V;
P72L, T90A, R250L, A311V;
P72L, T90A, V226I, A311V;
A40V, P72L, T90A, M229I, T273A, A311V;
A40V, P72L, T90A, M229I, F267L, T273A, A311V;
A40V, P72L, T90A, M184I, I193V, M229I, T273A, A311V;
A40V, P72L, T90A, V171L, M229I, T273A, A311V;
A40V, P72L, E82D, T90A, E209Q, M229I, L236V, V249I, T273A, A311V;
A40V, P72L, T90A, R182S, M229I, T273A, A311V;

A40V, P72L, T90A, A177V, M229I, T273A, A311V;
A40V, P72L, T90A, V171M, M229I, T273A, A311V;
A40V, P72L, T90A, M229I, S260G, T273A, A311V;
A40V, P72L, T90A, M229I, S251F, T273A, A311V;
A40V, P72L, T90A, V171L, M229I, F267L, T273A, A311V;
A40V, P72L, T90A, V171L, R182W, M229I, F267L, T273A, A311V;
A40V, P72L, T90A, V171L, R182W, M229I, F267L, T273A, A311V, N313D;
A40V, P72L, T90A, R91G, V171L, R182W, M229I, F267L, T273A, A311V;
A40V, P72L, T90A, V171L, R182W, M229I, G255D, F267L, A280S, T273A, A311V;
A40V, M53L, P72L, T90A, V171L, R182W, M229I, F267L, T273A, A311M;
A40V, P72L, T90A, V171L, R182W, M229I, A241V, F267L, T273A, V307A, A311V;
A40V, P72L, T90A, V171L, R182W, M229I, F267L, T273A, A311M;
A40V, P72L, T90A, T96S, I149T, V171L, R182W, M229I, F267L, T273A, A311V;
A40V, P72L, T90A, R91G, V171L, R182W, M229I, A241V, F267L, T273A, V307A, A311V; and
A40V, P72L, T90A, G108D, V171L, R182W, M229I, F267L, T273A, A311V.

7. The mutant hydroxylase of claim 5, comprising a set of amino acid substitutions selected from the group of sets of amino acid substitutions consisting of:
P72L, T90A, V206I, A210V, A311V;
P7L, P72L, T90A, A237V, A311V;
T51M, P72L, T90A, A311V;
A40V, P72L, T90A, A311V;
P72L, T90A, A237V, A311V;
P72L, T90A, M233I, A311V;
P72L, T90A, E258K, A311V;
P72L, T90A, F195L, A311V;
P72L, T90A, R250L, A311V;
P72L, T90A, V226I, A311V;
A40V, P72L, T90A, M229I, T273A, A311V;
A40V, P72L, T90A, M229I, F267L, T273A, A311V;
A40V, P72L, T90A, M184I, I193V, M229I, T273A, A311V;
A40V, P72L, T90A, V171L, M229I, T273A, A311V;
A40V, P72L, E82D, T90A, E209Q, M229I, L236V, V249I, T273A, A311V;
A40V, P72L, T90A, R182S, M229I, T273A, A311V;
A40V, P72L, T90A, A177V, M229I, T273A, A311V;
A40V, P72L, T90A, V171M, M229I, T273A, A311V;
A40V, P72L, T90A, M229I, S260G, T273A, A311V;
A40V, P72L, T90A, M229I, S251F, T273A, A311V;
A40V, P72L, T90A, V171L, M229I, F267L, T273A, A311V;
A40V, P72L, T90A, V171L, R182W, M229I, F267L, T273A, A311V;
A40V, P72L, T90A, V171L, R182W, M229I, F267L, T273A, A311V, N313D;
A40V, P72L, T90A, R91G, V171L, R182W, M229I, F267L, T273A, A311V;
A40V, P72L, T90A, V171L, R182W, M229I, G255D, F267L, A280S, T273A, A311V;
A40V, M53L, P72L, T90A, V171L, R182W, M229I, F267L, T273A, A311M;
A40V, P72L, T90A, V171L, R182W, M229I, A241V, F267L, T273A, V307A, A311V;
A40V, P72L, T90A, V171L, R182W, M229I, F267L, T273A, A311M;
A40V, P72L, T90A, T96S, I149T, V171L, R182W, M229I, F267L, T273A, A311V;
A40V, P72L, T90A, R91G, V171L, R182W, M229I, A241V, F267L, T273A, V307A, A311V; and
A40V, P72L, T90A, G108D, V171L, R182W, M229I, F267L, T273A, A311V.

8. A process for preparing a compound of formula (I), comprising:
reacting a compound of formula (II) with the mutant hydroxylase of claim 1 in the presence of α-ketoglutaric acid, ascorbic acid, and ferrous sulfate in an aqueous medium at temperature between 5 to 25° C. with pH 6 to 8;
wherein formulas (I) and (II) are:

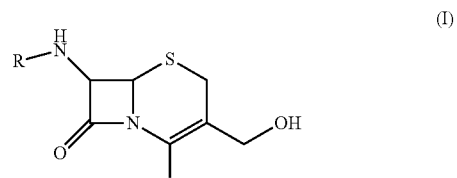

(I)

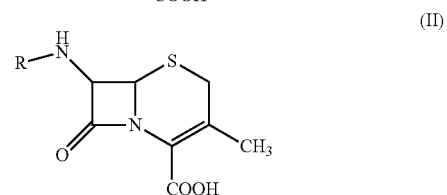

(II)

where R represents hydrogen, phenylacetyl, phenoxyacetyl, aminoadipoyl, or glutaryl.

9. A process for preparing a compound of formula (I), comprising:
reacting a compound of formula (II) with the mutant hydroxylase of claim 5 in the presence of α-ketoglutaric acid, ascorbic acid, and ferrous sulfate in an aqueous medium at temperature between 5 to 25° C. with pH 6 to 8;
wherein formulas (I) and (II) are:

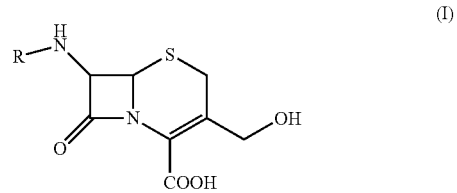

(I)

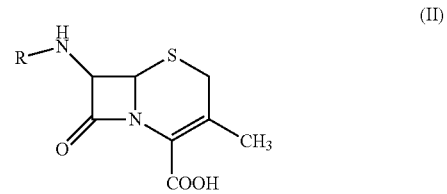

(II)

where R represents hydrogen, phenylacetyl, phenoxyacetyl, aminoadipoyl, or glutaryl.

* * * * *

SEQUENCE LISTING

<160> NUMBER OF SEQ ID NOS: 4

<210> SEQ ID NO 1
<211> LENGTH: 318
<212> TYPE: PRT
<213> ORGANISM: Streptomyces clavuligerus

<400> SEQUENCE: 1

```
Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr Gly Met Gly Val
                20                  25                  30

Phe Tyr Leu Thr Gly Tyr Gly Ala Gly Asp Lys Asp His Arg Leu Ala
            35                  40                  45

Thr Asp Thr Ala Met Asp Phe Phe Ala Asn Gly Thr Glu Ala Glu Lys
    50                  55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
        115                 120                 125

Ala Ala Ala Gln Glu Thr Ala Arg Leu Val Leu Thr Ala Ser Gly Gly
    130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205

Gln Ala Glu Ile Gly Gly Glu Leu Val Ser Leu Pro Val Val Glu Asp
    210                 215                 220

Ala Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
                245                 250                 255

Arg Glu Gly Ser Asp Arg Thr Ser Ser Val Phe Phe Leu Arg Pro Thr
            260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
    290                 295                 300

Asn Tyr Val Thr Met His Ala Lys Asn Glu Pro Gln Ala Gly
305                 310                 315
```

```
<210> SEQ ID NO 2
<211> LENGTH: 954
<212> TYPE: DNA
<213> ORGANISM: Streptomyces clavuligerus

<400> SEQUENCE: 2
atggcggaca cgcccgtacc gatcttcaac ctcgccgcac tgcgggaagg cgccgatcag      60
gagaagttcc gcgagtgcgt gaccgggatg ggggtcttct acctcaccgg gtacggcgcc     120
ggggataagg accaccggct ggccacggac acggcgatgg acttcttcgc gaacggcacc     180
gaggccgaga aggcggccgt gaccacggac gtcccgacca tgcggcgcgg ctactccgcg     240
ctggaggccg agagcaccgc ccaggtgacc aggaccggtt cctacacgga ctactcgatg     300
tccttctcca tgggcatctc gggcaacgtc ttcccctcgc cggagttcga gcgggtgtgg     360
acggagtact tcgacaagct ctacgcggcg gcccaggaga cggcgcggct ggtgctgacc     420
gcgagcggcg gctatgacgc ggagatcgtc ggaagcctgg acgagctgct ggacgccgac     480
cccgtgctgc ggctgcggta cttccccgag gtgcccgagc accggtccgc cgagcacgag     540
ccgcgccgga tggccccgca ctacgacctg tcgatcatca ccttcatcca ccagacgccg     600
tgcgccaacg gcttcgtcag cctccaggcc gagatcggcg gcgaactggt gagcctgccc     660
gtcgtggagg acgccgtcgt cgtgatgtgc ggcgcgatgg ccccgctggc gacccagggc     720
gcgctgcccg cgcccggca ccacgtccgg tccccggcg ccggtatgcg cgagggcagc     780
gaccgcacgt cgagcgtctt cttcctgcgc cccacgaccg acttctcgtt ctcggtggcc     840
aaggcccgca gctacggcct cgccgtcgac ctcgacatgg agacggccac cttcggcgac     900
tggatcggca ccaactacgt caccatgcac gcgaagaacg agccgcaggc cgga           954

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
gcatatggcg gacacgcccg tacc                                              24

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct

<400> SEQUENCE: 4
cccggcttga atgcaacgac gagcat                                            26
```